(12) United States Patent
Levin

(10) Patent No.: US 6,405,075 B1
(45) Date of Patent: Jun. 11, 2002

(54) APPARATUS AND METHOD OF FINDING THE DIASTOLIC BLOOD PRESSURE POINT USING PULSE OXIMETRY

(75) Inventor: Paul D. Levin, Santa Cruz, CA (US)

(73) Assignee: Palco Labs, Inc., Santa Cruz, CA (US)

( * ) Notice: Subject to any disclaimer, the term of this patent is extended or adjusted under 35 U.S.C. 154(b) by 0 days.

(21) Appl. No.: 09/677,950

(22) Filed: Oct. 2, 2000

Related U.S. Application Data

(60) Provisional application No. 60/157,712, filed on Oct. 5, 1999.

(51) Int. Cl.[7] .................................................. A61B 5/00
(52) U.S. Cl. ........................ 600/480; 600/485; 600/490
(58) Field of Search ................................. 600/490, 480, 600/485

(56) References Cited

U.S. PATENT DOCUMENTS

| | | | | |
|---|---|---|---|---|
| 4,776,339 A | * | 10/1988 | Schreiber | .................... 600/490 |
| 4,944,304 A | * | 7/1990 | Nishina | ....................... 600/490 |
| 5,172,696 A | * | 12/1992 | Souma | ........................ 600/480 |
| 5,423,322 A | * | 6/1995 | Clark et al. | .................. 600/480 |

* cited by examiner

Primary Examiner—Robert L. Nasser
(74) Attorney, Agent, or Firm—Bruce H. Johnsonbaugh

(57) ABSTRACT

An apparatus and method are provided for deriving diastolic blood pressure (DP) from systolic blood pressure (SP) and mean blood pressure (MP), especially useful in infants. A pulse oximeter is used to measure systolic blood pressure (SP) and an oscillametric blood pressure cuff is used to measure mean blood pressure (MP). Diastolic blood pressure is then derived from the formula:

$$DP = \frac{(MP \times K) - SP}{C}$$

where K is a constant of 2.94±0.04 and C is a constant of 2.06±0.04.

4 Claims, 1 Drawing Sheet

APPARATUS AND METHOD OF FINDING THE DIASTOLIC BLOOD PRESSURE POINT USING PULSE OXIMETRY

CROSS REFERENCE TO RELATED APPLICATION

This application claims the benefit of U.S. Provisional application Ser. No. 60/157,712 filed Oct. 5, 1999.

BACKGROUND AND BRIEF SUMMARY

The present invention relates to an apparatus and method of determining diastolic blood pressure, especially useful in neonates. The apparatus and method derive diastolic blood pressure (DP) from systolic blood pressure (SP) and mean blood pressure (MP) measurements obtained from a blood pressure cuff and a pulse oximeter probe on the same arm or leg.

The oscillometric method of determining blood pressure is almost universally used at this time by manufacturers of automatic blood pressure monitors. In this technique, a blood pressure cuff on a patient's arm or leg is pumped up to a level of at least 30 or 40 millimeters of mercury above the expected systolic blood pressure value. The cuff is then slowly deflated over a period of about 25 to 30 seconds. As air is gradually leaked out through a valve causing a pressure drop within the cuff, oscillations in air pressure begin to occur which are caused by the throbbing of the brachial or femoral artery under the cuff. It has been experimentally determined by many investigators that the point of maximum amplitude represents the mean pressure, also known as the time-averaged effective pressure. In 1969, Geddes discovered that it is the lowest pressure point for maximum cuff oscillations that best represents the true mean blood pressure value.

The systolic and diastolic points are determined non-invasively by oscillometry in various ways, most of which are proprietary. In general, however, diastolic and systolic accuracy necessitates good resolution of both the shape and amplitude of the oscillatory waves over the entire length of the pressure envelope. In general, it is thought necessary to determine the points of beginning and ending of pressure oscillations in addition to the shape of the oscillatory waves and it is particularly necessary to see the point at which oscillations suddenly begin to rise or suddenly begin to decrease in height. Generally, these points of sudden increase and decrease occur about 50 percent of the distance between the point of maximum oscillation and the point of disappearance of the oscillatory wave. Therefore, it is necessary to have good resolution of the entire pressure wave envelope to determine with accuracy the beginning and ending of oscillations to derive the systolic and diastolic blood pressure points. It is somewhat easier to determine the true mean pressure value since it is the point of maximum oscillation of the cuff. Even when the amplitude of the oscillations is small, this maximum point can usually be seen. For this reason, it is easier to determine mean arterial pressure than it is to obtain the systolic and diastolic blood pressure points.

Generally, the oscillometric method of determining blood pressure works well in adults but is less successful with very small subjects due to very low blood pressure in these patients and because of the small amplitude of the oscillometric waves in the brachial and femoral arteries.

For example, Chia and associates found that the oscillometric method was unreliable in infants when the mean arterial pressure was 35 millimeters or lower, which was fairly common among preterm newborn infants. The same conclusion was reached by Diprose and associates, who found that oscillometry failed to detect hypotension in very low birth weight infants. Wareham and associates reported that the oscillometric method in newborns underestimated systolic and mean blood pressure, and overestimated diastolic blood pressure.

Systolic blood pressure can also be obtained with a pulse oximeter and a blood pressure cuff by slowly raising the blood pressure cuff around a subject's arm or leg while simultaneously observing the pulse oximetry wave forms. Systolic pressure can be found at the point where pulse oximeter wave forms abruptly disappear. The reverse method can also be used by fully inflating the cuff and then slowly deflating while observing for the reappearance of the pulse wave form. The first appearance of the wave form is taken as the systolic blood pressure point.

When using the pulse oximetry technique for measuring systolic blood pressure in infants, Langbaum and Eyal found that oximetry gave excellent systolic blood pressure measurements when compared to simultaneous intra-arterial readings. Systolic pressure points could be determined accurately in every case in a series of 51 preterm infants with pulse oximetry. By contrast, the standard oscillometric method failed completely in three infants and had systolic inaccuracies of as much as 16 mm of mercury.

While pulse oximetry is useful for measuring the systolic blood pressure point, it gives no information regarding either diastolic or mean pressure. Diastolic measurements are needed in pediatric cases to evaluate arteriovenous shunts, congenital heart disease, and cases of pulmonary hypertension. Therefore, the pulse oximetry alone for measuring blood pressure has somewhat limited application.

It should be stated that the systolic blood pressure point in adults, in contrast to neonates, cannot always be measured accurately with a pulse oximeter. It has been found that in approximately 20% of adult subjects the so-called systolic blood pressure point is from 10 to 20 points low as compared with the systolic point derived from Korotkoff sounds over the brachial artery. It must therefore be assumed that in at least some adult patients, vasospasm causes a delay in opening of the peripheral circulation. This phenomenon of delayed opening of the arterioles seems not to occur in neonates.

The six references, cited at page 7 below, are hereby incorporated by reference as though set forth in full.

The present invention makes use of the pulse oximeter to measure the systolic blood pressure point which has been found to be accurate in infants, but in addition adds the oscillometric technique of determining mean blood pressure which has been found to be reliable since it relies on the point of maximum oscillation which can be generally found even in the smallest infant. Mean arterial pressure represents the time averaged pressure within the arterial system. Diastole typically lasts approximately two-thirds of the entire cardiac cycle and therefore the mean pressure value is closer to the diastolic value than the systolic value. Since systolic pressure can be accurately found in infants with pulse oximetry, and because mean pressure can be inferred from the point of maximum impulse, diastolic pressure can be determined using a variation of a relationship which has been known for many years, namely, that systolic pressure plus twice the diastolic pressure divided by three gives a close approximation of mean pressure. This formula has generally been used for determining mean blood pressure when diastolic and systolic pressure are derived from oscillometry. The rationale for the formula is described by Daily & Schroeder in *Techniques in Bedside Hemodynamic Monitoring* published by C. V. Mosby Co.

The present invention has its best application in neonatology where conventional oscillometric monitoring is difficult because of the very small size of these patients. It was therefore thought advantageous to determine the systolic/diastolic/mean relationship as closely as possible in this particular patient population.

Data from actual intra-arterial pressure measurements was kindly supplied by Michael Langbaum, M.D. from the neonatal ICU of Johns Hopkins Hospital. This data, from 49 neonatal patients, reproduced in Table 1 on page 8, showed that the best diastolic pressure value could be derived from a small alteration of the general formula, possibly due to a slightly longer diastolic phase in neonates as opposed to adults. The best mean value was obtained by using the formula $$1) \quad MP = \frac{SP + (DP \times 2.06)}{2.94}$$

In this case, systolic and diastolic pressures were taken from the intra-arterial readings and mean pressure was the unknown. When mean and systolic values were taken from the intra-arterial readings and diastolic pressure was the unknown, the formula was changed to:;

$$2) \quad DP = \frac{(MP \times 2.94) - SP}{2.06}$$

This approach resulted in calculated diastolic values very close to the diastolic values measured intra-arterially (Table 1). When intra-arterial systolic and mean values were used with formula (2), the average calculated positive diastolic variance was only 1.4 mm of mercury and the average negative variance was 1.5 mm of mercury (Table 1). Since systolic pressures can be accurately determined in infants by pulse oximetry, as proven by Langbaum and others, and since mean pressures can be accurately determined in newborns by observing the point of maximum cuff impulse, this invention provides an improved apparatus and method for non-invasively determining the diastolic blood pressure of neonates.

DETAILED DESCRIPTION OF THE DRAWING

Figure 1:
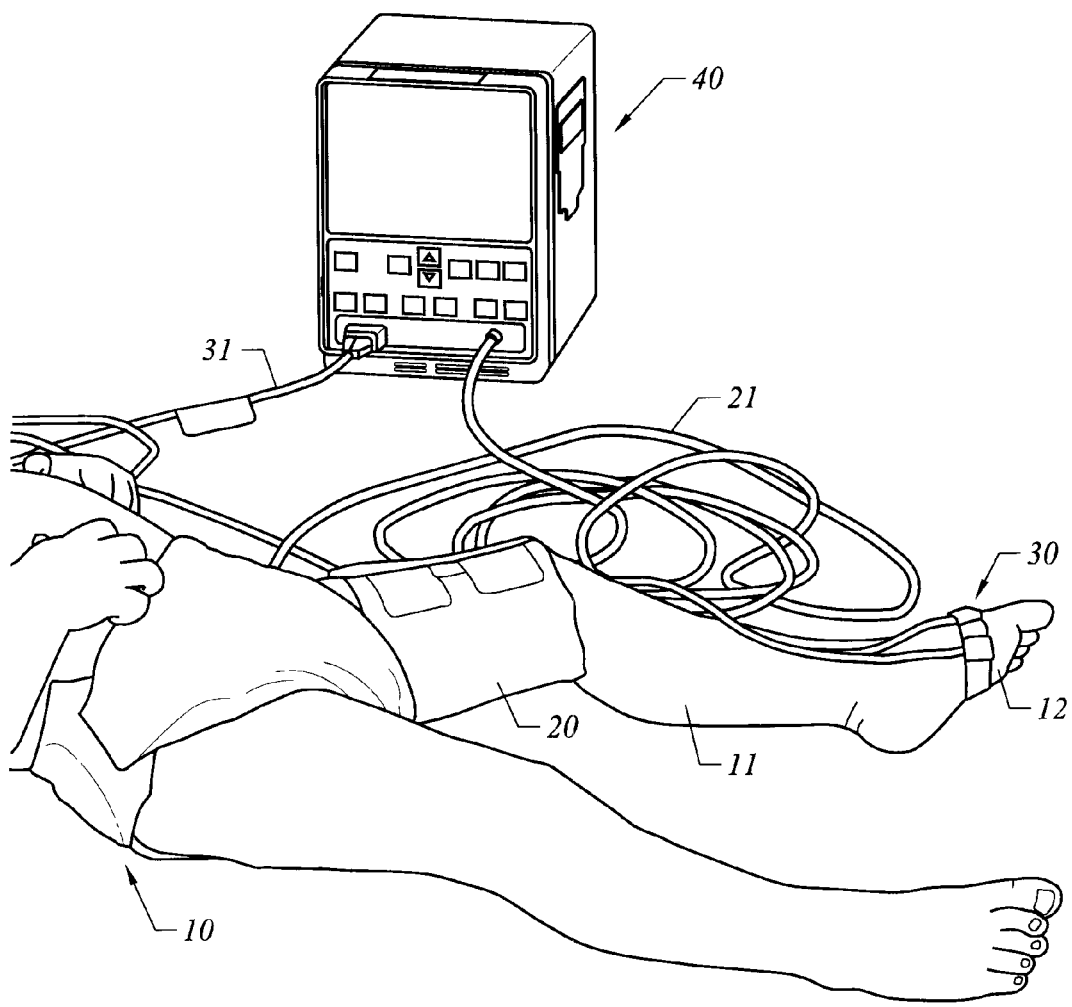
FIG. 1 is a perspective view of the apparatus according to the present invention, showing its use on an infant.

FIG. 1 shows the legs and mid-section of an infant 10. A standard oscillometric blood pressure cuff 20 is applied to the thigh of the infant's left leg 11. An air hose 21 connects the cuff 20 to a vital signs monitor 40 known in the industry. A pulse oximetry sensor 30 is applied to the infant's left foot 12. The sensor 30 may be of the type shown in U.S. Pat. No. 5,991,648, incorporated herein by reference. A sensor cable 31 connects the sensor 30 to vital signs monitor 40. The present invention combines mean blood pressure, found from the point of maximum oscillations in the cuff 20, with the systolic point found with pulse oximetry sensor 30 to derive diastolic pressure as discussed above. Systolic, mean, and diastolic pressures can then be displayed on the monitor, along with other vital signs. It has been determined that equation (2) provides the most accurate diastolic blood pressure readings for neonates and that the constants have a range of ±0.04. However, the invention may be utilized for patients in general. In that case, it has been determined that the mean blood pressure MP should be multiplied by a constant K between 2.7 and 3.1. The denominator of the right hand side of equation (2) should be a constant C between 1.9 and 2.1.

REFERENCES CITED

1. J. A. Posey, MSME; L A Geddes, M E, PhD; H. Williams, B S; and A G Moore, "The Meaning of the Point of Maximum Oscillations in Cuff Pressure in the Indirect Measurement of Blood Pressure., Part 1," *Cardiovascular Research Center Bulletin*, July-September, 1969.
2. L. A. Geddes, M. Voelz, C. Combs, D. Reiner, and C. F. Babbs, "Characterization of the Oscillometric Method for Measuring Indirect Blood Pressure," *Annals of Biomedical Engineering*, Vol. 10, pp. 271–280, 1982.
3. Michael Langbaum, MD, and Fabien G. Eyal, MD, "A Practical and Reliable Method of Measuring Blood Pressure in the Neonate by Pulse Oximetry," *The Journal of Pediatrics*, October 1994.
4. F. Chia, MBBS; A. T. Ang, MBBS; Tze-Wai Wong, MBBS; K. W. Tan, MBBS; Kam-pui Fung, MBBS, MRCP, DCH; J. Lee, PhD; Khin Khin, MBBS; "Reliability of the Dinamap Non-invasive Monitor in the Measurement of Blood Pressure of 111 Asian Newborns," *Clinical Pediatrics*, Vol. 29 No. 5, May 1990.
5. John A. Wareham, MD; Larry D. Haugh, PhD; Scott B. Yeager, M D; Jeffrey D. Horbar, M D; "Prediction of Arterial Blood Pressure in the Premature Neonate Using the Oscillometric Method," *AJDC*, Vol 141, October 1987.
6. G K Diprose, D H Evans, L N J Archer, and M I Levene, "Dinamap fails to detect hypotension in very low birthweight infants," *Archives of Disease in Childhood*, 1986, 61, 771–773.

Patient LA systolic, diastolic, and mean blood pressure values courtesy of Michael Longbaum, M.D., Neonatal ICU, Johns Hopkins Medical Center

| Systolic | Diastolic | Mean | Calculated Diastolic DP = ((MP*2.94) − SP)/2.06 | Positive Variance | Negative Variance |
|---|---|---|---|---|---|
| 44 | 37 | 40 | 35.7 | | −1.3 |
| 53 | 31 | 41 | 32.8 | 1.8 | |
| 41 | 28 | 34 | 28.6 | 0.6 | |
| 45 | 30 | 37 | 31.0 | 1.0 | |
| 62 | 36 | 50 | 41.3 | 5.3 | |
| 36 | 23 | 30 | 25.3 | 2.3 | |
| 33 | 20 | 26 | 21.1 | 1.1 | |
| 42 | 37 | 38 | 33.8 | | −3.2 |
| 55 | 44 | 49 | 43.2 | | −0.8 |
| 82 | 51 | 64 | 51.5 | 0.5 | |
| 56 | 38 | 45 | 37.0 | | −1.0 |
| 47 | 28 | 37 | 30.0 | 2.0 | |
| 46 | 36 | 40 | 34.8 | | −1.2 |
| 42 | 29 | 33 | 26.7 | | −2.3 |
| 43 | 27 | 34 | 27.7 | 0.7 | |
| 53 | 30 | 39 | 29.9 | | −0.1 |
| 73 | 43 | 56 | 44.5 | 1.5 | |
| 66 | 41 | 50 | 39.3 | | −1.7 |
| 66 | 36 | 48 | 36.5 | 0.5 | |
| 55 | 30 | 41 | 31.8 | 1.8 | |
| 73 | 41 | 52 | 38.8 | | −2.2 |
| 50 | 31 | 40 | 32.8 | 1.8 | |
| 50 | 34 | 42 | 35.7 | 1.7 | |

-continued

Patient LA systolic, diastolic, and mean blood pressure values courtesy of Michael Longbaum, M.D., Neonatal ICU, Johns Hopkins Medical Center

| Systolic | Diastolic | Mean | Calculated Diastolic DP = ((MP*2.94) − SP)/2.06 | Positive Variance | Negative Variance |
|---|---|---|---|---|---|
| 49 | 32 | 40 | 33,3 | 1.3 | |
| 60 | 42 | 50 | 42.2 | 0.2 | |
| 52 | 32 | 41 | 33.3 | 1.3 | |
| 43 | 37 | 40 | 36.2 | | −0.8 |
| 54 | 42 | 48 | 42.3 | 0.3 | |
| 49 | 22 | 33 | 23.3 | 1.3 | |
| 61 | 41 | 49 | 40.3 | | −0.7 |
| 57 | 35 | 48 | 40.8 | 5.8 | |
| 74 | 50 | 61 | 51.1 | 1.1 | |
| 55 | 36 | 43 | 34.7 | | −1.3 |
| 52 | 37 | 44 | 37.6 | 0.6 | |
| 59 | 47 | 52 | 45.6 | | −1.4 |
| 48 | 33 | 40 | 33.8 | 0.8 | |
| 73 | 42 | 54 | 41.6 | | −0.4 |
| 58 | 42 | 49 | 41.8 | | −0.2 |
| 59 | 33 | 42 | 31.3 | | −1.7 |
| 61 | 45 | 53 | 46.0 | 1.0 | |
| 47 | 29 | 37 | 30.0 | 1.0 | |
| 65 | 39 | 46 | 34.1 | | −4.9 |
| 47 | 31 | 38 | 31.4 | 0.4 | |
| 43 | 34 | 39 | 34.8 | 0.8 | |
| 55 | 34 | 43 | 34.7 | 0.7 | |
| 57 | 35 | 43 | 33.7 | | −1.3 |
| 72 | 40 | 51 | 37.8 | | −2.2 |
| Average Positive and Negative Variance of Calculated Diastolic | | | | 1.4 | −1.5 |

What is claimed is:

1. Apparatus for determining diastolic blood pressure comprising;
   pulse oximetry means for determining systolic blood pressure (SP),
   oscillometric blood pressure cuff means for determining mean blood pressure (MP) and
   means for combining said determined values for systolic blood pressure (SP) and mean blood pressure (MP) to derive diastolic blood pressure (DP) by the following formula:

$$DP = \frac{(MP \times K) - SP}{C}$$

where K is a constant between 2.7 and 3.1 and wherein C is a constant between 1.9 and 2.1.

2. Apparatus for determining diastolic blood pressure in neonates comprising;
   pulse oximetry means for determining systolic blood pressure (SP),
   oscillometric blood pressure cuff means for determining mean blood pressure (MP) and
   means for combining said determined values for systolic blood pressure (SP) and mean blood pressure (MP) to derive diastolic blood pressure (DP) by the following formula:

$$DP = \frac{(MP \times K) - SP}{C}$$

where K is a constant of 2.94±0.04 and C is a constant of 2.06±0.04.

3. A method for determining diastolic blood pressure comprising the steps:
   determining systolic blood pressure (SP) by using a pulse oximeter,
   determining mean blood pressure (MP) by using oscillometry with a blood pressure cuff,
   determining diastolic blood pressure (DP) from said systolic blood pressure (SP) and mean blood pressure (MP) by the following mathematical formula:

$$DP = \frac{(MP \times K) - SP}{C}$$

where K is a constant between 2.7 and 3.1 and wherein C is a constant between 1.9 and 2.1.

4. A method of determining diastolic blood pressure in neonates comprising the steps:
   determining systolic blood pressure (SP) by using a pulse oximeter,
   determining mean blood pressure (MP) by using oscillometry with a blood pressure cuff,
   determining diastolic blood pressure (DP) from said systolic blood pressure (SP) and mean blood pressure (MP) by the following mathematical formula:

$$DP = \frac{(MP \times K) - SP}{C}$$

where K is a constant of 2.94±0.04 and C is a constant of 2.06±0.04.

* * * * *